United States Patent [19]
Dyer et al.

[11] Patent Number: 6,156,900
[45] Date of Patent: Dec. 5, 2000

[54] RACEMIZATION OF PRECURSORS TO LEVOBUPIVACAINE AND ANALOGUES THEREOF

[75] Inventors: Ulrich Conrad Dyer; Martin Woods, both of Cambridge; Raymond McCague, Cambridgeshire, all of United Kingdom

[73] Assignee: Darwin Discovery Limited, United Kingdom

[21] Appl. No.: 09/250,473

[22] Filed: Feb. 12, 1999

Related U.S. Application Data

[63] Continuation of application No. 08/817,687, Apr. 7, 1997, abandoned.

[30] Foreign Application Priority Data

Oct. 7, 1994 [GB] United Kingdom .................. 9420245
Mar. 10, 1995 [GB] United Kingdom .................. 9504924

[51] Int. Cl.⁷ ............................................. C07D 211/40
[52] U.S. Cl. ............................ 546/233; 562/401
[58] Field of Search .................. 546/233; 562/401

[56] References Cited

U.S. PATENT DOCUMENTS

| | | | |
|---|---|---|---|
| 3,796,750 | 3/1974 | Schubel .................. | 562/401 |
| 4,602,096 | 7/1986 | Karrenbauer .............. | 498/498 |
| 4,638,086 | 1/1987 | Grabley .................. | 562/401 |
| 4,647,692 | 3/1987 | Jacewicz ................. | 562/401 |
| 4,695,576 | 9/1987 | AfEkenstam .............. | 514/330 |
| 5,733,754 | 3/1998 | Wisdon ................... | 435/106 |

FOREIGN PATENT DOCUMENTS

| | | |
|---|---|---|
| 0137371 | 4/1985 | European Pat. Off. . |
| 0173921 | 3/1986 | European Pat. Off. . |
| 0175840 | 4/1986 | European Pat. Off. . |
| 2074022 | 10/1971 | France . |

OTHER PUBLICATIONS

Rodwell "Pipecolic acid" methods in Enz. v. XVIIB, Aca. Press, p. 174–188, 1971.

McDermott et al. "N–methylamino acids in peptide synthesis . . . " Can. J. chem. vol. 51, p. 2562–70, 1973.

Rodwell "Pipecolic acid" CA 76:55563, 1971.

McDermott et al. "N–methylamino acids in peptide synthesis . . . " CA 79:105551, 1973.

Scott, "Drug stereochemistry" Eds Wainer, p. 183–187, 1993.

Hongo, C. et al. (1981) "Asymmetric Transformation of N–Acyl–DL–Amino Acids" Bulletin of The Chemical Society of Japan 54 (11):3286–3290.

Chenault, H. K., et al. (1989) "Kinetic Resolution of Unnatural and Rarely Occurring Amino Acids: Enantioselective Hydrolysis of N–acyl Amino Acids Catalysed by Acylase I" Journal of the American Chemical Soc. 111(16):6354–6364.

*Primary Examiner*—Celia Chang
*Attorney, Agent, or Firm*—Saliwanchik, Lloyd & Saliwanchik

[57] ABSTRACT

A process for the preparation of optically-enriched pipecolic acid as a salt with an optically-active acid, comprises asymmetric transformation of pipecolic acid, as a racemic mixture of a mixture enriched in the opposite enantiomer from that desired, with the optically-active acid in a solvent comprising an acid that causes racemisation, in the absence of aldehyde.

9 Claims, No Drawings

RACEMIZATION OF PRECURSORS TO LEVOBUPIVACAINE AND ANALOGUES THEREOF

CROSS-REFERENCE TO RELATED APPLICATION

This application is a continuation of co-pending application Ser. No. 08/817,687, filed Apr. 7, 1997.

FIELD OF INVENTION

This invention relates to a process for the racemisation of N-acylamino-acids.

BACKGROUND OF THE INVENTION

N-acylamino-acids are useful in the pharmaceutical industry. Process for their racemisation are known; see Bull. Chem. Soc. Jpn. 60:649–652 (1987), 56:3744–3747 (1983), 60:4321–4323 (1987), 66:965–970 (1992), 66:2430–1437 (1992), and 64:191–195 (1991); and Agr. Biol. Chem. 43:395 (1979).

The known process generally require either specialised equipment or the use of reagents which are not applicable to industrial processes. For example, Hongo et al, Bull. Chem. Soc. Jpn. 54:3386 (1981), describe the use of chloroform and acetic anhydride for the racemisation of N-butanoyl-proline. This would clearly have a high environmental impact if carried out on a commercial scale.

SUMMARY OF THE INVENTION

The present invention is based on the surprising discovery that, quite simply, dehydrating conditions allow N-acyl-α-amino-acids to racemise, e.g. by conversion of a compound of the formula R—CO—NR$^2$—COOH from optically-enriched to racemic form. This represents an advantageous process over the prior art.

DESCRIPTION OF THE INVENTION

In the racemisation reaction of the invention, it is generally preferred that R, R$^1$ and R$^2$ each represent the same or different alkyl groups (optionally-substituted) or R$^1$ and R$^2$ together represent a ring structure. The nature of these substituents is not critical, provided of course that they do not interfere with the process. Such substituents will not usually have more than 20 C atoms.

A particular example of the invention is the case where R is methyl and Y is a 4-carbon ring system, in which case the product is N-acetylpipecolic acid.

The dehydrating conditions may be provided by acid, e.g. an organic or mineral acid, often an inert (co)solvent. A preferred embodiment of the invention utilises 4-toluenesulphonic acid in toluene. The amount of acid may be catalytic. Without wishing to be bound by theory, it may be that the reaction of the invention proceeds via an azlactone intermediate.

Alternatively, an orthoester such as orthoformate or orthoacetate, e.g. trimethyl orthoacetate, can be used, introducing the COR group in the reaction. Thus, the starting material may be N-unsubstituted, e.g. R$^2$HN—CHR$^1$—COOH (optically-active) can be converted to R—CO—NR$^2$—CHR$^1$—COOH (racemate). The reagent is preferably used in a stoichiometric amount. This reaction may be conducted with azeotropic removal of water.

The starting material may be prepared by any suitable resolution process, examples of which are well known to those skilled in that art. A particularly useful biotransformation process is described in WO-A-9510604.

An important aspect of this invention relates to the ability to operate the process of an industrial scale. This in turn means that the optically-enriched (N-acyl)amino-acids themselves, e.g. obtained by resolution but to an extent that may be insufficiently enantiopure for immediate use, become useful products. This applies particularly to mixtures of enantiomers in which one, often the (R)-enantiomer, is present in an enantiomeric excess of 20 to 80%, preferably 25 to 75%, more preferably 30 to 70%, and most preferably 35 to 65%, with respect to its optical antipode. For example, a mixture enriched in the (R)-enantiomer can be used practically, by racemisation and subsequent resolution. The desired product, e.g. (S)-N-acylpipecolic acid, can be converted to levobupivacaine by methods that will be evident to those skilled in the art.

Crystallisation to a pure racemate and possible dynamic resolutions with chiral salts are other benefits and applications. N-acylpipecolic acids are useful in the synthesis of analgesics such as levobupivacaine and ropivicaine, e.g. by racemisation of an optically-enriched mixture, resolution, reaction with 2,6-dimethylaniline and N-alkylation. All there reaction may be conducted by known methodology.

The following Examples illustrate the invention.

EXAMPLE 1

(R)-N-acetylpipecolic acid was placed in 10 volumes of toluene and heated, with stirring, to reflux. On attaining reflux, a catalytic amount of 4-toluenesulphonic acid was added to the solution which was then left to reflux for two hours with stirring. After this time had elapsed, the toluene was removed by rotary evaporation. To the residual solid was added 10 volumes of distilled water; this was then extracted with methyl ethyl ketone (MEK) (3×10 vols) to leave the sulphonic acid in the aqueous layer with any pipecolic acid formed. The MEK extracts were then concentrated down to a solid on the rotary evaporator to give racemic-N-acetylpipecolic acid, with 97% recovery.

EXAMPLE 2

(S)-pipecolic acid (1.0 g, 7.7 mmol) was treated with trimethyl orthoacetate (15 ml, 171 mmol, 22 eq. 15 vol) and methanol (5 ml, 5 vol). The mixture was stirred and heated for 48 h and then concentrated in vacuo. The residue was dissolved in dichloromethane (10 ml) and filtered through a silica gel plug to yield N-acetylpipecolic acid, methyl ester (730 mg, 50%) which was racemic by GC analysis and had a $^1$H nmr spectrum which compared favourably with authentic material.

What is claimed is:

1. A process fore racemising an optically-active N-acylamino-acid having the formula R—CO—NR$^2$—CHR$^1$—COOH wherein R$^1$ and R$^2$ complete a heterocyclic ring, which comprises reaction of the N-acylamino-acid under reflux with a catalytic amount of a catalytic acid, in an inert solvent, such that water is removed, wherein said catalytic acid is a sulphonic acid.

2. The process according to claim 1, wherein the catalytic acid is separated from the N-acylamino-acid using water.

3. The process according to claim 1, wherein the catalytic acid is 4-toluenesulphonic acid.

4. The process according to claim 1, wherein the N-acylamino-acid is a N-acylpipecolic acid.

5. A process for preparing levobupivacaine, which comprises resolution of a racemate of a N-acylpipecolic acid, separating the (S)-N-acylpipecolic-acid and converting it to levobupivacaine; and racemising the (R)-N-acylpipecolic acid by a process according to claim 1.

6. A process for preparing a ropivacaine, which comprises resolution of a racemate of a N-acylpipecolic acid, separating the (S)-N-acylpipecolic-acid and converting it to ropivacaine; and racemising the (R)-N-acylpipecolic acid by a process according to claim 1.

7. The process according to claim 5, wherein the converting step comprises reaction with 2,6-dimethylaniline and alkylation with a butylating agent.

8. The process according to claim 6, wherein the converting step comprises reaction with 2,6-dimethylaniline and alkylation with a propylating agent.

9. A mixture of enantiomers of an optically-active N-acylpipecolic-acid, in which the (R)-enantiomer is in an excess of 20 to 80% with respect to its optical antipode.

* * * * *

UNITED STATES PATENT AND TRADEMARK OFFICE
CERTIFICATE OF CORRECTION

PATENT NO. : 6,156,900
DATED : December 5, 2000
INVENTOR(S) : Ulrich Conrad Dyer, Martin Woods and Raymond McCague It is certified that error appears in the above-identified patent and that said Letters Patent is hereby corrected as shown below:

Column 2,
Line 53, "fore" should read -- for --.

Signed and Sealed this

Twenty-eighth Day of May, 2002

*Attest:*

*Attesting Officer*

JAMES E. ROGAN
*Director of the United States Patent and Trademark Office*